United States Patent
Qian et al.

(10) Patent No.: US 9,058,651 B2
(45) Date of Patent: Jun. 16, 2015

(54) SYSTEM AND METHODS FOR FUNCTIONAL ANALYSIS OF SOFT ORGAN SEGMENTS IN SPECT-CT IMAGES

(75) Inventors: Jian-Zhong Qian, Princeton Junction, NJ (US); Xiaolan Zeng, Princeton, NJ (US); Guo-Qing Wei, Plainsboro, NJ (US); Li Fan, Belle Mead, NJ (US)

(73) Assignees: EDDA TECHNOLOGY, INC., Princeton, NJ (US); EDDA TECHNOLOGY (SUZHOU) LTD., Suzhou, Jiangsu (CN)

( * ) Notice: Subject to any disclaimer, the term of this patent is extended or adjusted under 35 U.S.C. 154(b) by 542 days.

(21) Appl. No.: 13/343,053

(22) Filed: Jan. 4, 2012

(65) Prior Publication Data
US 2012/0207268 A1 Aug. 16, 2012

Related U.S. Application Data

(60) Provisional application No. 61/429,638, filed on Jan. 4, 2011.

(51) Int. Cl.
| | |
|---|---|
| G06K 9/00 | (2006.01) |
| G06T 7/00 | (2006.01) |
| A61B 6/03 | (2006.01) |
| A61B 6/00 | (2006.01) |

(52) U.S. Cl.
CPC .............. *G06T 7/0014* (2013.01); *A61B 6/032* (2013.01); *A61B 6/037* (2013.01); *A61B 6/481* (2013.01); *A61B 6/5217* (2013.01); *A61B 6/5247* (2013.01); *G06T 7/0028* (2013.01); *G06T 2207/10081* (2013.01); *G06T 2207/10108* (2013.01); *G06T 2207/30056* (2013.01)

(58) Field of Classification Search
None
See application file for complete search history.

(56) References Cited

U.S. PATENT DOCUMENTS

| | | | |
|---|---|---|---|
| 6,337,998 B1 * | 1/2002 | Behl et al. ..................... | 607/101 |
| 6,505,629 B1 * | 1/2003 | Mikus et al. ................... | 128/898 |
| 6,745,613 B2 * | 6/2004 | Rendahl et al. .............. | 73/35.02 |
| 7,738,683 B2 * | 6/2010 | Cahill et al. .................. | 382/128 |
| 7,822,248 B2 * | 10/2010 | Ikemoto ........................ | 382/128 |
| 7,933,440 B2 * | 4/2011 | Littmann ....................... | 382/131 |
| 2002/0120260 A1 * | 8/2002 | Morris et al. .................... | 606/41 |
| 2003/0216310 A1 * | 11/2003 | Thornton et al. ............... | 514/12 |
| 2005/0065421 A1 * | 3/2005 | Burckhardt .................... | 600/407 |
| 2006/0052687 A1 * | 3/2006 | Ruohonen ..................... | 600/410 |
| 2006/0110071 A1 * | 5/2006 | Ong et al. ...................... | 382/294 |
| 2006/0120584 A1 * | 6/2006 | Hillman ......................... | 382/128 |
| 2007/0036402 A1 * | 2/2007 | Cahill et al. ................... | 382/128 |
| 2007/0081706 A1 * | 4/2007 | Zhou et al. ..................... | 382/128 |

(Continued)

OTHER PUBLICATIONS

Reitinger, B. et al. "Liver Surgery Planning Using Virtual Reality" Virtual and Augmented Reality Supported Simulators, Computer Graphics and Applications, IEEE (vol. 26, Issue: 6) Nov.-Dec. 2006, pp. 36-47.*

(Continued)

*Primary Examiner* — Chan Park
*Assistant Examiner* — Mia M Thomas
(74) *Attorney, Agent, or Firm* — Pillsbury Winthrop Shaw Pittman LLP

(57) ABSTRACT

An analysis system and method for measuring soft organ functions in general and the liver specifically utilizing both measurement and imaging devices such as a SPECT system and a CT system. The two images utilize a common coordinate system and segment the liver image for enhanced functional analysis.

19 Claims, 5 Drawing Sheets

(56) References Cited

U.S. PATENT DOCUMENTS

| | | | |
|---|---|---|---|
| 2008/0033291 A1* | 2/2008 | Rousso et al. | 600/436 |
| 2008/0050347 A1* | 2/2008 | Ichim | 424/93.7 |
| 2008/0097186 A1* | 4/2008 | Biglieri et al. | 600/407 |
| 2009/0097726 A1* | 4/2009 | Rusko et al. | 382/131 |
| 2009/0257628 A1* | 10/2009 | Ranga et al. | 382/128 |
| 2010/0027861 A1* | 2/2010 | Shekhar et al. | 382/131 |
| 2010/0111386 A1* | 5/2010 | El-Baz | 382/128 |
| 2010/0316268 A1* | 12/2010 | Liang et al. | 382/128 |
| 2011/0046451 A1* | 2/2011 | Horn et al. | 600/300 |
| 2011/0224553 A1* | 9/2011 | Stothers et al. | 600/473 |
| 2012/0053443 A1* | 3/2012 | Sakuragi | 600/407 |
| 2012/0242350 A1* | 9/2012 | Sundaresan et al. | 324/629 |
| 2013/0084246 A1* | 4/2013 | Moats et al. | 424/9.3 |

OTHER PUBLICATIONS

International Search Report corresponding to PCT/US12/20126 dated May 1, 2012.

* cited by examiner

SYSTEM AND METHODS FOR FUNCTIONAL ANALYSIS OF SOFT ORGAN SEGMENTS IN SPECT-CT IMAGES

CROSS REFERENCE TO RELATED APPLICATIONS

This application claims priority from U.S. Provisional Application No. 61/429,638 filed Jan. 4, 2011 the disclosure of which is incorporated herein by reference in its entirety.

TECHNICAL FIELD

The present teaching relates generally to system and methods for functional analysis of soft organs in medical imaging. More specifically, the present teaching relates to methods and system for computerized functional analysis of soft organs in general and liver segments specifically using SPECT-CT images

BACKGROUND

Computerized Tomography or CT modality has been widely used for diagnosis purposes. It can provide very detailed anatomical structures of human organs. In oncology, CT is used to monitor therapeutic responses of a treatment to tumors by measuring size changes. However, it may take a long time, e.g., several months, for a treatment to be reflected in the size change of a tumor. Contrastingly, Single Photon Emission Computed Tomography ("SPECT") is a modality that can provide immediate metabolic measurement of a human organ and/or tumors, allowing one to discriminate healthy tissue from diseased tissue at the functional level. However, while both SPECT and CT devices provides imaging, the imaging from the SPECT device cannot provide the detailed anatomical structural information about the human organs the way CT does. Recently, however, CT and SPECT have been combined into one imaging device, allowing both CT and SPECT images to be taken in one image session.

Currently, the utilization of SPECT-CT imaging stays mostly at the image level. For example, in liver functional measurement in SPECT, physicians usually manually trace the left and right lobe boundaries of the liver in SPECT and compute the isotope counts to measure the lobe's liver functions. However, in percutaneous treatment planning for liver lesions, such as by Radio-Frequency Ablation (RFA) or chemoembolization, it is desirable to measure liver functions in local regions or interested lobe segments. For example, it is desirable to measure the liver function of a blood supply or blood drainage territory of a vascular structure. Since SPECT does not provide information about detailed anatomical structures, operating with the SPECT images alone cannot perform the above task. Although SPECT and CT image devices may provide mechanical registration between the SPECT image space and CT image space, the transformation may only be used for a rough alignment of the SPECT and CT images. Since SPECT and CT images are acquired in different time, breathing and body motion can cause non-rigid deviation from the mechanical registration. Thus, analysis in the CT space cannot be readily applied to the SPECT space.

It is therefore highly desirable to be able to accurately measure the liver functions of a local region or liver segments in SPECT by using anatomical information in CT. It is also desirable to perform such measurement in real-time and in an interactive manner.

SUMMARY

In an embodiment of the present disclosure, a system for measuring liver function is disclosed. The system comprises a first device for generating a functional image of a liver and a second device for generating a structural image of the liver. The system includes a coordinate transformation unit for transforming a point coordinate from the second device into a point coordinate of the first device and creating a liver image based on the transforming, a segmentation unit for segmenting the liver image; and an analysis unit for analyzing the segmented liver functions.

In another embodiment the first device is a Single Photon Emission Computed Tomography (SPECT) device. In another embodiment, the second device is a Computerized Axial Tomography (CT) device.

In another embodiment, the first device further comprises a diseased tissue specification unit and a healthy tissue segmentation unit and the imaging unit of the second device further comprises an organ segmentation unit and an organ analysis unit. In still another embodiment, the diseased liver specification unit and the healthy tissue segmentation unit determine surface points of healthy liver tissue.

In another embodiment, the system includes a healthy tissue registration unit. In another embodiment, the healthy tissue registration unit determines the local deformation parameters based on the healthy liver tissue. In another embodiment, the organ segmentation unit and the regional analysis unit perform organ geometrical analysis based on vascular structures.

In another embodiment a method implemented on a machine having at least one processor, storage, and a communication platform connected to a network for analyzing functions of a liver is disclosed. The method includes identifying liver tissue using a first device, identifying diseased liver tissue using information obtained from the first device, identifying healthy liver tissue using information obtained from the first device, obtaining surface points of the healthy liver tissue, segmenting the liver using images obtained from a second device, identifying internal structures of the liver from the imaging system, obtaining surface points of the liver tissue using the images obtained from the second device, mapping the surface points of the healthy liver tissue obtained using the first device to the surface points of the liver tissue obtained using the second device, and analyzing the liver functions of local regions. In another embodiment the analyzing is based on the mapping of the surface points of the healthy liver tissue obtained using the first device.

In another embodiment, the analyzing is based on the areas of the identified internal structures from the second device. In another embodiment the areas of internal structures from the second device are mapped to the coordinate space of the first device.

In another embodiment the analyzing is based on identifying the isotope count within a specific region. In another embodiment the analysis is performed by computing the isotope count within the specific region divided by the total isotope count within the whole liver region. In another embodiment of the method, the first device is a Single Photon Emission Computed Tomography (SPECT) device. In another embodiment of the method, the second device is a Computerized Axial Tomography (CT) device.

In another embodiment a machine-readable tangible and non-transitory medium, having information for analyzing a liver during a medical procedure, recorded thereon is disclosed. The machine-readable tangible and non-transitory medium when read by the machine, causes the machine to identify liver tissue using a first device, identify diseased liver tissue using information obtained from the first device; identify healthy liver tissue using information obtained from the first device, obtaining surface points of the healthy liver tissue, segment the liver using images obtained from a second device, identify internal structures of the liver from images from the second device, obtain surface points of the liver tissue using the images obtained from the second device, map the surface points of the healthy liver tissue obtained using the first device to the surface points of the liver tissue obtained using the second device, and analyze the liver functions.

In an embodiment of the present disclosure, a system for measuring soft organ function is disclosed. The system comprises a first device for generating a functional image of a soft organ and a second device for generating a structural image of the soft organ. The system includes a coordinate transformation unit for transforming a point coordinate from the second device into a point coordinate of the first device and creating a soft organ image based on the transforming, a segmentation unit for segmenting the soft organ image, and an analysis unit for analyzing the functions of the segmented soft organ.

In another embodiment a method implemented on a machine having at least one processor, storage, and a communication platform connected to a network for analyzing functions of a soft organ is disclosed. The method includes identifying soft organ tissue using a first device, identifying diseased soft organ tissue using information obtained from the first device, identifying healthy liver tissue, obtaining surface points of the healthy liver tissue, segmenting the soft organ using images obtained from a second device, identifying internal structures of the soft organ from images obtained from the second device, obtaining surface points of the soft organ tissue using the images obtained from the second device, mapping the surface points of the healthy soft organ tissue obtained using the first device to the surface points of the soft organ tissue obtained using the imaging system, and analyzing the functions of soft organ for local regions.

BRIEF DESCRIPTION OF THE DRAWINGS

The inventions claimed and/or described herein are further described in terms of embodiments. These embodiments are described in detail with reference to the drawings. These embodiments are non-limiting embodiments, in which like reference numerals represent similar structures throughout the several views of the drawings, and wherein:

DETAILED DESCRIPTION

The present disclosure teaches a system and methods for liver functional analysis in SPECT at the regional level in terms of advanced geometrical analysis of the liver in CT images. The teaching combines functional image and anatomical images to achieve more accurate and localized functional analysis. Not intended as a limitation of any sort, however, the present disclosure references a liver as the soft organ. It is to be understood, surgery and procedures on any organs such as heart, lungs, kidneys, stomach, intestines, brain, or other soft organs may utilize and benefit from the present disclosure. Accordingly, for ease of clarity, the liver is used to describe the system and method of the present disclosure, but, as will be understood by those skilled in the art, it is not intended to limit the scope of the invention in any manner.

Figure 1:
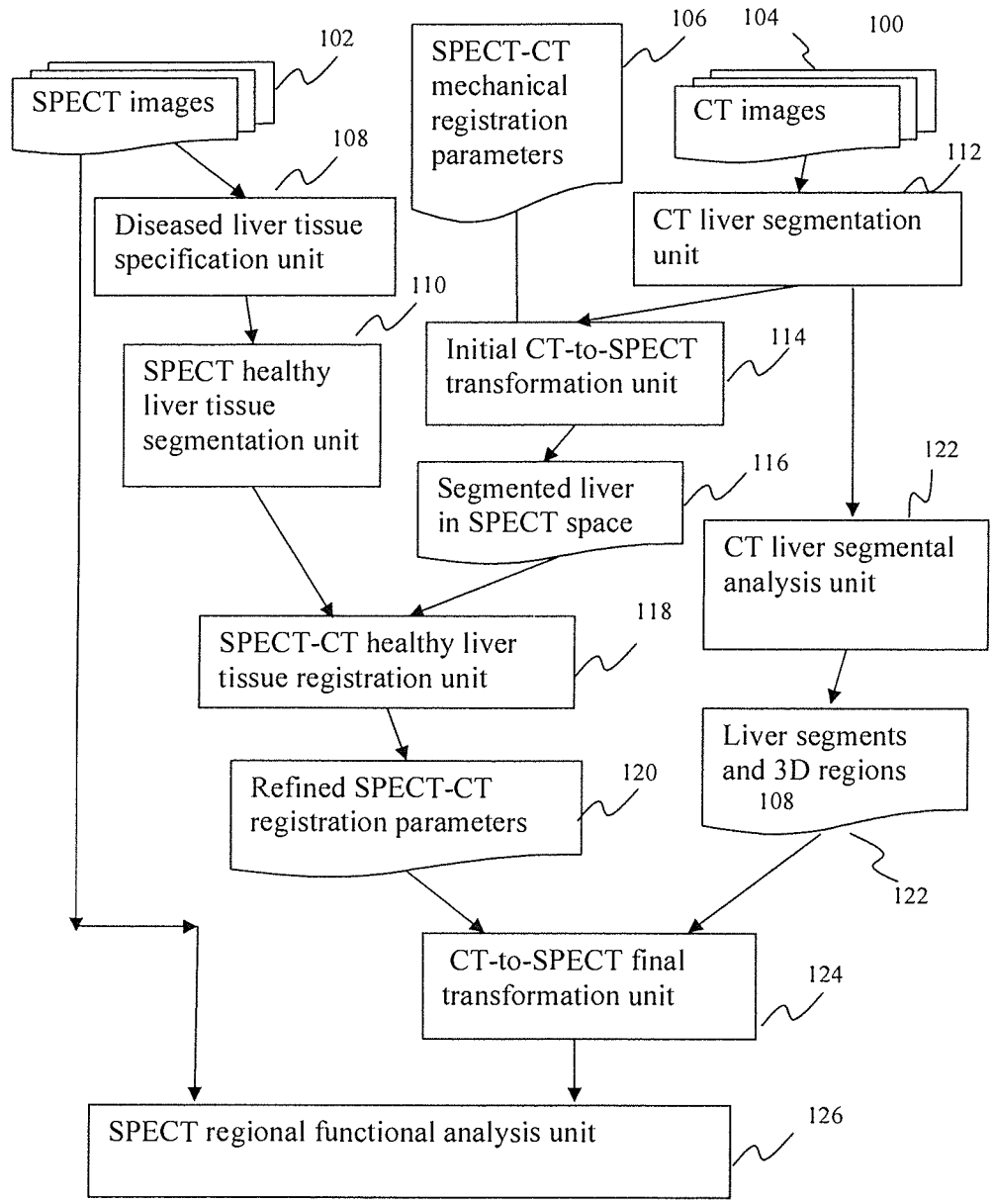
FIG. 1 depicts a system diagram for functional analysis of liver segments for treatment planning and treatment monitoring.

FIG. 1 shows a system diagram of a liver regional functional analysis system 100. The system may consist of a SPECT diseased liver tissue specification unit 108, a SPECT healthy liver segmentation unit 110, a CT liver segmentation unit 112, an initial SPECT-to-CT transformation unit 114, SPECT-CT healthy liver tissue registration unit 118, a CT liver segmental analysis unit 122, a refined CT-to-SPECT final transformation unit 124, a SPECT regional functional analysis unit 126.

The geometrical relationship between SPECT and CT coordinate system is described by the SPECT-CT mechanical registration parameters 106, which transforms a point in the CT coordinate system into the SPECT coordinate system by the initial CT-to-SPECT transformation unit 114. The output of unit 114 is the liver object transformed into the SPECT image space 116. The SPECT diseased liver specification unit 108 and SPECT healthy liver segmentation unit 110 determines the surface points of healthy liver tissue. The SPECT-CT healthy liver tissue registration unit 118 determines the local deformation parameters based on the healthy SPECT liver tissue and the healthy CT liver tissue. The output of unit 118 is a set of refined SPECT-CT registration parameters 120 that takes into account both the mechanical registration and the local deformations between the SPECT and CT acquisitions. The liver segmental and regional analysis unit 122 performs CT liver geometrical analysis based on vascular structures in CT images.

For example, a blood supply territory analysis of a certain branch of a hepatic portal vein may be performed by this unit to obtain the blood supply region of that specific branch. The output of unit 122 is one or more multiple 3D regions of the liver organ. The refined CT-to-SPECT transformation unit 124 may map the 3D regions in CT space into the SPECT space based on both the mechanical transformation and refined registration parameters.

After the interested regions and segments are transformed into the SPECT image space, functional analysis of such regions may be performed by the SPECT regional functional analysis unit 126. In SPECT, functional analysis of a segment may be performed by computing the isotope count (brightness summation) within the region divided by the total isotope count within the whole liver region.

Figure 2A:
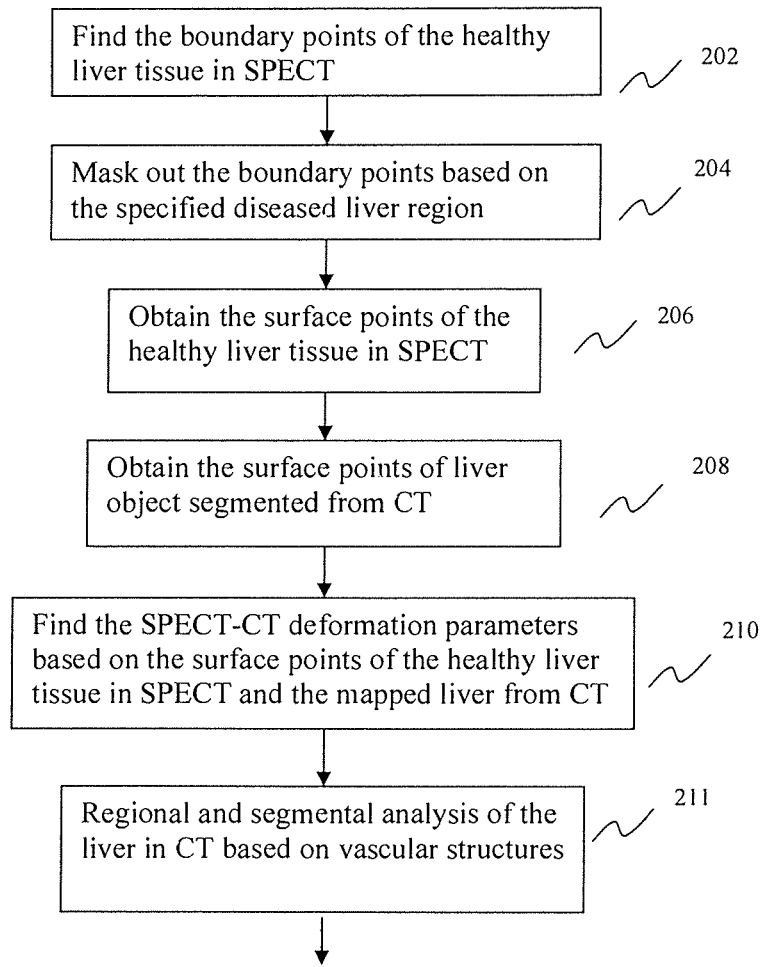
FIGS. 2(a)-2(b) depict a flow diagram according to one embodiment of the present teaching for functional analysis of liver segments for treatment planning and treatment monitoring.
Figure 2B:
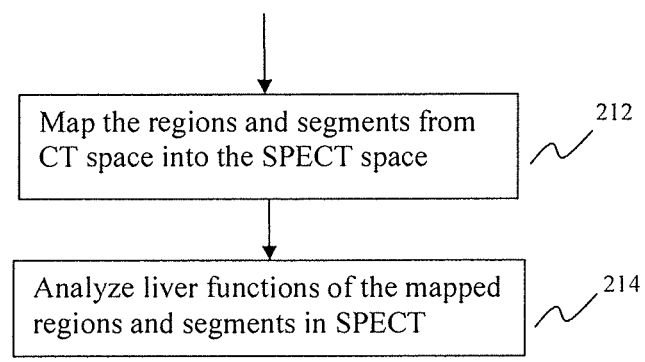
Figure 3A:
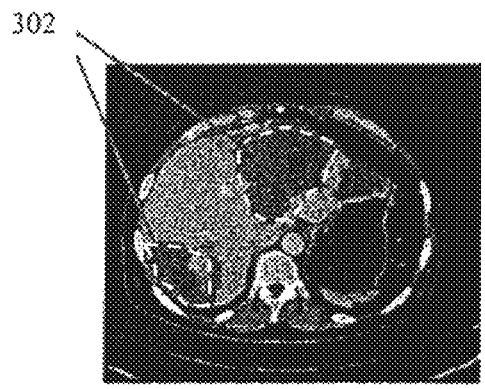
FIGS. 3(a)-3(d) depict mapping of anatomical analysis result in CT to SPECT.
Figure 3B:
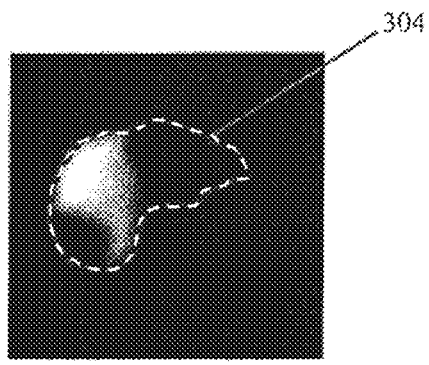
Figure 3C:
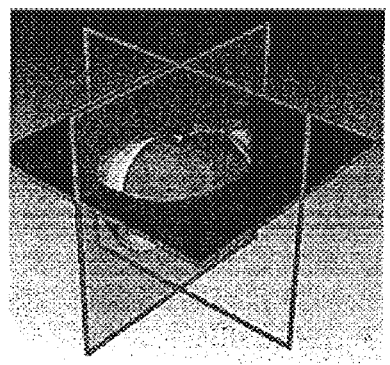
Figure 3D:
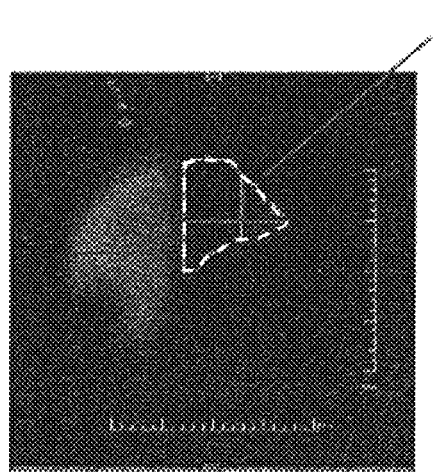

FIGS. 2 (a) and (b) show a flow diagram of FIG. 1, according to an embodiment of the present disclosure. First, diseased liver tissue is specified in SPECT images. In SPECT images, diseased liver tissue has no liver function and does not show high uptake values, i.e., shows low or no intensity values. Such diseased regions need to be excluded in the registration procedure. The specification of diseased liver tissue in SPECT images may be performed, at step 202, either manually by tracing out the low intensity portion of the liver organ in the images, or automatically by identifying low intensity regions. Healthy liver tissue may be segmented out or masked at step 204 using simple thresholding. This may be done manually or automatically. In the manual mode, the thresholds may be specified by the user through a user interface. In the automatic mode, the threshold may be determined by histogram analysis of the SPECT images. Pixels whose intensities are above a certain predetermined threshold may be segmented as healthy liver tissues. After diseased and healthy liver tissues are segmented out, points on the liver surface that belong to the healthy tissue may be determined by taking out the common boundary points among diseased and healthy tissue from the boundary points of the healthy liver tissue. At step 206, the liver is segmented from the CT images, using any method known to one of ordinary skill in the art, such as those described in US Patent Application 2007/0055455 "Methods for interactive liver disease diagnosis" by Guo-Qing Wei et. al. The segmented liver voxels are transformed into the SPECT image space at step 208 based on the SPECT-CT mechanical registration parameters. At step 210, local registration parameters between liver organs in the SPECT and CT acquisitions are computed based on the surface points of the healthy liver tissue in the SPECT and the transformed segmented liver from the CT. Deformable registration methods based on spline or thin-plate model may be used for this purpose. The above process may be performed interactively in such a way as to allow the user to adjust the threshold in segmenting diseased and healthy liver tissue, the registration may be updated using updated surface points of the healthy liver tissue. At step 211, regional and segmental analysis is performed utilizing the CT image. For example, by selecting a specific branch of a vascular structure, such as a portal vein, the blood supply region of that branch may be identified using any known method such as those described in U.S. Pat. No. 7,840,044 "Method and system for liver lobe segmentation and pre-operative surgical planning" by Feng Ma et al.

In another embodiment, regional/segmental analysis provides important information about treatment planning, such as liver resection, in which the resection area may be determined based on lesion size and spatial relationship between lesion and vascular structures. At step 212, the obtained region of interest may be mapped into the SPECT image space based on the SPECT-CT mechanical registration parameters and the local deformation parameters. With the mapped region of interest in the SPECT image space, functional analysis of that region of interest may be performed, at step 214, based on the isotope count in the region of interest and the count in the whole liver volume. For example, the ratio of the isotope count in the region of interest to the isotope count in the whole liver may be computed as a measure of liver function of the region of interest. In another embodiment, the SPECT images may be acquired at different time intervals to form a dynamic SPECT image sequence. In that case, the change of isotope count as a function of time within the region of interest may be used to compute the function of region of interest.

FIG. 3 shows examples of the mapping between SPECT and CT image space for liver segments. FIG. 3(*a*) is one slice of a CT liver image sequence, where area 302 indicates diseased liver regions. FIG. 3(*b*) shows a slice of the SPECT image at the same location of the liver as the CT image, where 304 shows the liver boundary found from CT images mapped onto the SPECT image space. The diseased areas shows no uptake in the SPECT image. FIG. 3(*c*) shows the result of 3D segment analysis of the liver organ obtained from the CT images, where different colors or shades represent different liver segments. Segmental analysis of the liver may be performed using methods known in the art, such as those based on vascular structures. FIG. 3(*d*) shows the mapped liver segments overlaid on one slice of the SPECT image, where 306 indicates the mapped segment boundaries. In liver transplantation or resection, the remnant liver function may be computed as the ratio of the remaining lobe or segment after treatment to the whole liver volume in CT. This assumes that the function of the liver is homogenous in both the diseased and the healthy liver segments. This may not be true. With the liver segments mapped onto the SPECT image space, the remnant liver function may be more accurately computed as ratio of the isotope counts in the remaining lobe to the isotope count in the whole liver.

In treatment monitoring or follow-up, SPECT may be used to measure the functional recovery of the liver organ or progression of liver diseases, such as chronic viral hepatitis. The total isotope count may first be computed from the SPECT images of the injection syringe before injection. A series of SPECT images may be taken for the liver organ at different times. Then liver boundaries obtained from CT liver segmentation may be mapped to each of the SPECT series and used to compute the total isotope count in the liver organ in each series. The accumulated isotope count in the liver may be displayed as a curve, with the x-axis being the time and the y-axis the percent of the liver isotope count in the total isotope count. This curve may be compared with the curve of the normal liver to quantify the liver function and evaluate disease progression. In one embodiment, the summation of slopes at each point of the curve may be used to quantify the functional activity of the liver. The same analysis may be performed for a specific liver region to evaluate the functional recovery of that region. The region may be defined in the CT image space and mapped to the SPECT image space.

Figure 4:
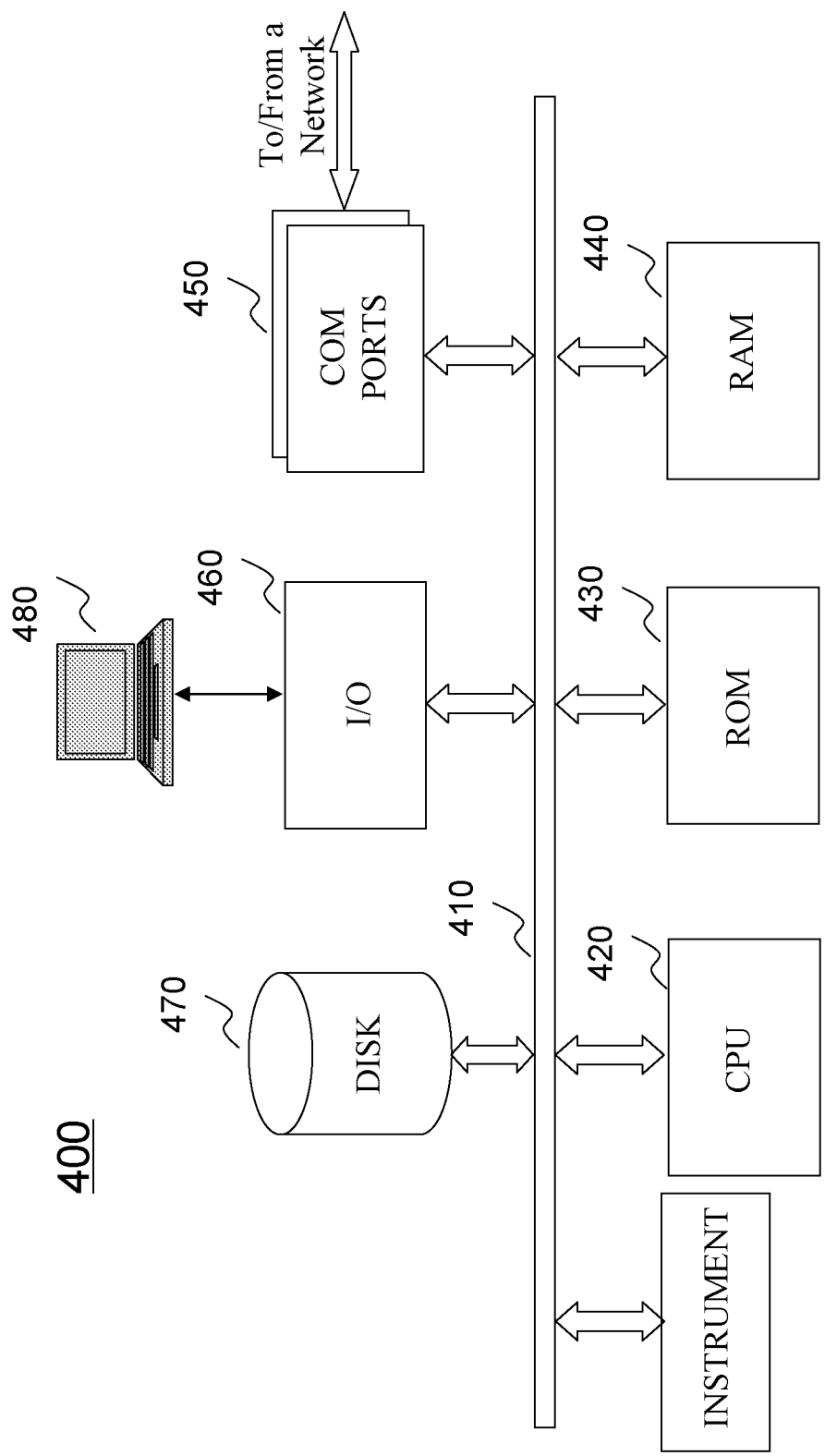
FIG. 4 depicts a computer system for carrying out the system and method of the present disclosure in accordance with the present disclosure.

FIG. 4 depicts a general computer architecture on which the present teaching can be implemented and has a functional block diagram illustration of a computer hardware platform which includes user interface elements. The computer may be a general purpose computer or a special purpose computer. This computer 400 can be used to implement any components of the functional analysis using SPECT-CT imaging as described herein. For example, the image display, image storing, image processing, can all be implemented on a computer such as computer 400, via its hardware, software program, firmware, or a combination thereof. Although only one such computer is shown, for convenience, the computer functions relating to the disclosure described herein may be implemented in a distributed fashion on a number of similar platforms, to distribute the processing load.

The computer 400, for example, includes COM ports 450 connected to and from a network connected thereto to facilitate data communications. The computer 400 also includes a central processing unit (CPU) 420, in the form of one or more processors, for executing program instructions. The exemplary computer platform includes an internal communication bus 410, program storage and data storage of different forms, e.g., disk 470, read only memory (ROM) 430, or random access memory (RAM) 440, for various data files to be processed and/or communicated by the computer, as well as possibly program instructions to be executed by the CPU. The computer 400 also includes an I/O component 460, supporting input/output flows between the computer and other components therein such as user interface elements 480. The computer 400 may also receive programming and data via network communications.

Hence, aspects of functional analysis of liver segmentation in SPECT-CT imagery as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution. In addition, the functional analyses utilizing SPECT-CT imagery as disclosed herein can be implemented as a firmware, firmware/software combination, firmware/hardware combination, or a hardware/firmware/software combination.

While the inventions have been described with reference to the certain illustrated embodiments, the words that have been used herein are words of description, rather than words of limitation. It is understood that various modifications may be made herein and that the subject matter disclosed may be implemented in various forms and examples, and that the teachings may be applied in numerous applications, only some of which have been described herein. Changes may be made, within the purview of the appended claims, without departing from the scope and spirit of the invention in its aspects. Although the disclosure has been described herein with reference to particular structures, acts, and materials, the present disclosure is not to limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A method implemented on a machine having at least one processor, storage, and a communication platform connected to a network for analyzing functions of a liver, the method comprising:
   obtaining one or more images of liver tissue of the liver by a first device;
   identifying diseased liver tissue from the images obtained by the first device;
   identifying healthy liver tissue from the images obtained by the first device;
   obtaining a first set of surface points of the healthy liver tissue based on boundaries of the identified diseased and healthy liver tissues;
   segmenting the liver based on one or more images obtained by a second device;
   obtaining a second set of surface points of the liver tissue based on the images obtained by the second device;
   computing one or more deformation parameters based on the first set of surface points and the second set of surface points;
   identifying one or more regions of interest in the liver from the images obtained by the second device;
   mapping the one or more regions of interest to the coordinate space of the first device; and
   analyzing liver functions of the mapped one or more regions of interest based on the images obtained by the first device.

2. The method of claim 1, wherein the analyzing is based on the mapping of the first set of surface points of the healthy liver tissue.

3. The method of claim 1, further comprising:
   identifying internal structures of the liver based on the images obtained by the second device;
   wherein the analyzing is based on areas of the identified internal structures.

4. The method of claim 3, wherein the areas of internal structures are mapped to the coordinate space of the first device.

5. The method of claim 3, wherein the analyzing is based on identifying an isotope count within a specific region.

6. The method of claim 5, wherein the analyzing is based on computing the isotope count within the specific region divided by the total isotope count within the whole liver region.

7. The method of claim 1, wherein the first device is a Single Photon Emission Computed Tomography device.

8. The method of claim 1, wherein the second device is a Computerized Axial Tomography (CT) device.

9. The method of claim 1, wherein the analyzing includes summing slopes at each of a series of points of a curve to quantify the liver functions.

10. A machine-readable tangible and non-transitory medium, having information recorded thereon for analyzing functions of a liver, wherein the information, when read by the machine, causes the machine to perform the following:
   obtaining one or more images of liver tissue of the liver by a first device;
   identifying diseased liver tissue from the images obtained by the first device;
   identifying healthy liver tissue from the images obtained by the first device;

obtaining a first set of surface points of the healthy liver tissue based on boundaries of the identified diseased and healthy liver tissues;

segmenting the liver based on one or more images obtained by a second device;

obtaining a second set of surface points of the liver tissue based on the images obtained by the second device;

computing one or more deformation parameters based on the first set of surface points and the second set of surface points;

identifying one or more regions of interest in the liver from the images obtained by the second device;

mapping the one or more regions of interest to the coordinate space of the first device; and analyzing liver functions of the mapped one or more regions of interest based on the images obtained by the first device.

11. A system for analyzing functions of a liver, comprising:

a first imaging device configured for obtaining one or more images of liver tissue of the liver;

a diseased liver tissue specification unit configured for identifying diseased liver tissue from the images obtained by the first device;

a healthy liver tissue segmentation unit configured for
identifying healthy liver tissue from the images obtained by the first device, and
obtaining a first set of surface points of the healthy liver tissue based on boundaries of the identified diseased and healthy liver tissues;

a segmentation unit configured for
segmenting the liver based on one or more images obtained by a second device, and
obtaining a second set of surface points of the liver tissue using the images obtained by the second device;

a healthy liver tissue registration unit configured for computing one or more deformation parameters based on the first set of surface points and the second set of surface points;

a liver segmental analysis unit configured for identifying one or more regions of interest in the liver from the images obtained by the second device;

a transformation unit configured for mapping the one or more regions of interest to the coordinate space of the first device; and a functional analysis unit configured for analyzing liver functions of the mapped one or more regions of interest based on the images obtained by the first device.

12. The system of claim 11, wherein the analyzing is based on the mapping of the first set of surface points of the healthy liver tissue.

13. The system of claim 11, wherein
the liver segmental analysis unit is further configured for identifying internal structures of the liver based on the images obtained by the second device; and
the analyzing is based on areas of the identified internal structures.

14. The system of claim 13, wherein the areas of internal structures are mapped to the coordinate space of the first device.

15. The system of claim 13, wherein the analyzing is based on identifying an isotope count within a specific region.

16. The system of claim 15, wherein the analyzing is based on computing the isotope count within the specific region divided by the total isotope count within the whole liver region.

17. The system of claim 11, wherein the first device is a Single Photon Emission Computed Tomography device.

18. The system of claim 11, wherein the second device is a Computerized Axial Tomography (CT) device.

19. The system of claim 11, wherein the analyzing includes summing slopes at each of a series of points of a curve to quantify the liver functions.

\* \* \* \* \*